United States Patent
Stauffer

(10) Patent No.: US 6,204,418 B1
(45) Date of Patent: Mar. 20, 2001

(54) PROCESS FOR THE CHLORNATION OF HYDROCARBONS

(76) Inventor: John E. Stauffer, 6 Pecksland Rd., Greenwich, CT (US) 06831

( * ) Notice: Subject to any disclaimer, the term of this patent is extended or adjusted under 35 U.S.C. 154(b) by 0 days.

(21) Appl. No.: 09/360,974

(22) Filed: Jul. 27, 1999

Related U.S. Application Data

(63) Continuation-in-part of application No. 09/136,557, filed on Aug. 19, 1998, now abandoned, which is a continuation-in-part of application No. 08/500,299, filed on Jul. 10, 1995, now abandoned, which is a continuation-in-part of application No. 08/303,114, filed on Sep. 7, 1994, now abandoned.

(51) Int. Cl.$^7$ .............................. C07C 17/08; C07C 17/15
(52) U.S. Cl. .................... 570/242; 570/243; 570/260; 570/261; 570/123; 570/163
(58) Field of Search .................................... 570/242, 243, 570/260, 261, 123, 163; 568/893

(56) References Cited

U.S. PATENT DOCUMENTS

| | | |
|---|---|---|
| 4,088,704 | 5/1978 | Nychka et al. . |
| 5,017,732 | 5/1991 | Zawalski . |
| 5,099,084 | 3/1992 | Stauffer . |
| 5,416,246 | 5/1995 | Krespan et al. . |

FOREIGN PATENT DOCUMENTS 555080  7/1977  (RU) .

*Primary Examiner*—Alan Siegel
(74) *Attorney, Agent, or Firm*—Young & Basile, P.C.

(57) ABSTRACT

A process is provided for the chlorination of aliphatic hydrocarbons containing 1 to 4 carbon atoms using hydrogen chloride as the source of chlorine. The process comprises reaction steps operated in tandem in separate zones. First, an unsaturated aliphatic fluorocarbon is oxychlorinated to give the corresponding saturated perchlorofluorocarbon and water, and second, the saturated perchlorofluorocarbon is reacted in the vapor phase with a hydrocarbon to produce the desired chlorinated hydrocarbon, hydrogen chloride and the unsaturated aliphatic fluorocarbon, third, hydrogen chloride and unsaturated aliphatic fluorocarbon are separated from the chlorinated hydrocarbon and recycled to the first step, and fourth, the chlorinated hydrocarbon is further purified by subjecting it to addition chlorination to convert traces of unsaturated aliphatic fluorocarbon to the corresponding saturated perchlorofluorocarbon, which is separated and recycled to the second step.

9 Claims, 1 Drawing Sheet

PROCESS FOR THE CHLORNATION OF HYDROCARBONS

CROSS-REFERENCE TO RELATED APPLICATION

This application is a continuation-in-part of U.S. patent application Ser. No. 09/136,557, filed Aug. 19, 1998, entitled "Process for the Chlorination of Hydrocarbons" now abandoned, which is a continuation-in-part of U.S. patent application Ser. No. 08/500,299 filed Jul. 10, 1995, entitled "Process for the Chlorination of Hydrocarbons" now abandoned, which in turn is a continuation-in-part of U.S. patent application Ser. No. 08/303,114 filed Sep. 7, 1994, entitled "Process for the Chlorination of Hydrocarbons" now abandoned.

FIELD OF THE INVENTION

This invention relates to a novel method of chlorinating aliphatic hydrocarbons containing 1 to 4 carbon atoms using hydrogen chloride as the source of chlorine. The principal products are monochlorinated compounds such as methyl chloride and allyl chloride as well as polychlorinated compounds, for example chloroform and ethylene dichloride. The process has a distinct advantage of providing high yields of chlorinated hydrocarbons. In addition, it offers significant cost savings over existing technology.

BACKGROUND OF THE INVENTION

Processes have been disclosed for the chlorination of hydrocarbons using hydrogen chloride as the source of chlorine in U.S. Pat. Nos. 4,899,000; 4,990,696; 5,097,083; 5.099,084; and 5,185,479. These processes have several features in common. They all rely on the oxychlorination of perchloroethylene with hydrogen chloride and oxygen to produce hexachloroethane. In a separate reaction zone, the hexachloroethane so produced is reacted with a hydrocarbon to yield a chlorinated hydrocarbon, hydrogen chloride and perchloroethylene. By recycling the hydrogen chloride and perchloroethylene produced in the second step to the oxychlorination reaction, a continuous process can be achieved.

The advantages of these processes over the prior art are significant. By conducting the chemical reactions in two segregated zones, the hydrocarbon feed is chlorinated in the absence of oxygen or air. Thus, combustion is avoided and the production of unwanted byproducts minimized. Furthermore, these processes rely on the use of conventional equipment, the characteristics of which are well known.

Notwithstanding the advantages of these existing processes, certain drawbacks are apparent. Hexachloroethane sublimes at about 187° C., which requires that it must be heated above this temperature to transport it, or a solvent such as perchloroethylene is needed. Furthermore, even though the hexachloroethane is sealed within the system, its relative toxicity is a potential hazard.

Finally, the equilibrium between the dehalogenation of hexachloroethane and its regeneration from perchloroethylene may constrain the operating conditions of the process. The oxychlorination reaction temperature must be maintained sufficiently low in order to favor the formation of hexachloroethane. At higher temperatures, the hexachloroethane will decompose to perchloroethylene and chlorine.

Therefore it is an object of the present invention to provide a new chlorinating agent or family of compounds that do not possess the disadvantages of hexachloroethane. These compounds can function as chlorine carriers enabling the transfer of chlorine from one reaction zone to another. These compounds must be convenient to handle and be effective in the process. They cannot sacrifice any of the positive features of hexachloroethane.

These and other objects, features, and advantages of the invention will be apparent from the following description and the accompanying drawing.

SUMMARY OF THE INVENTION

Figure 1:
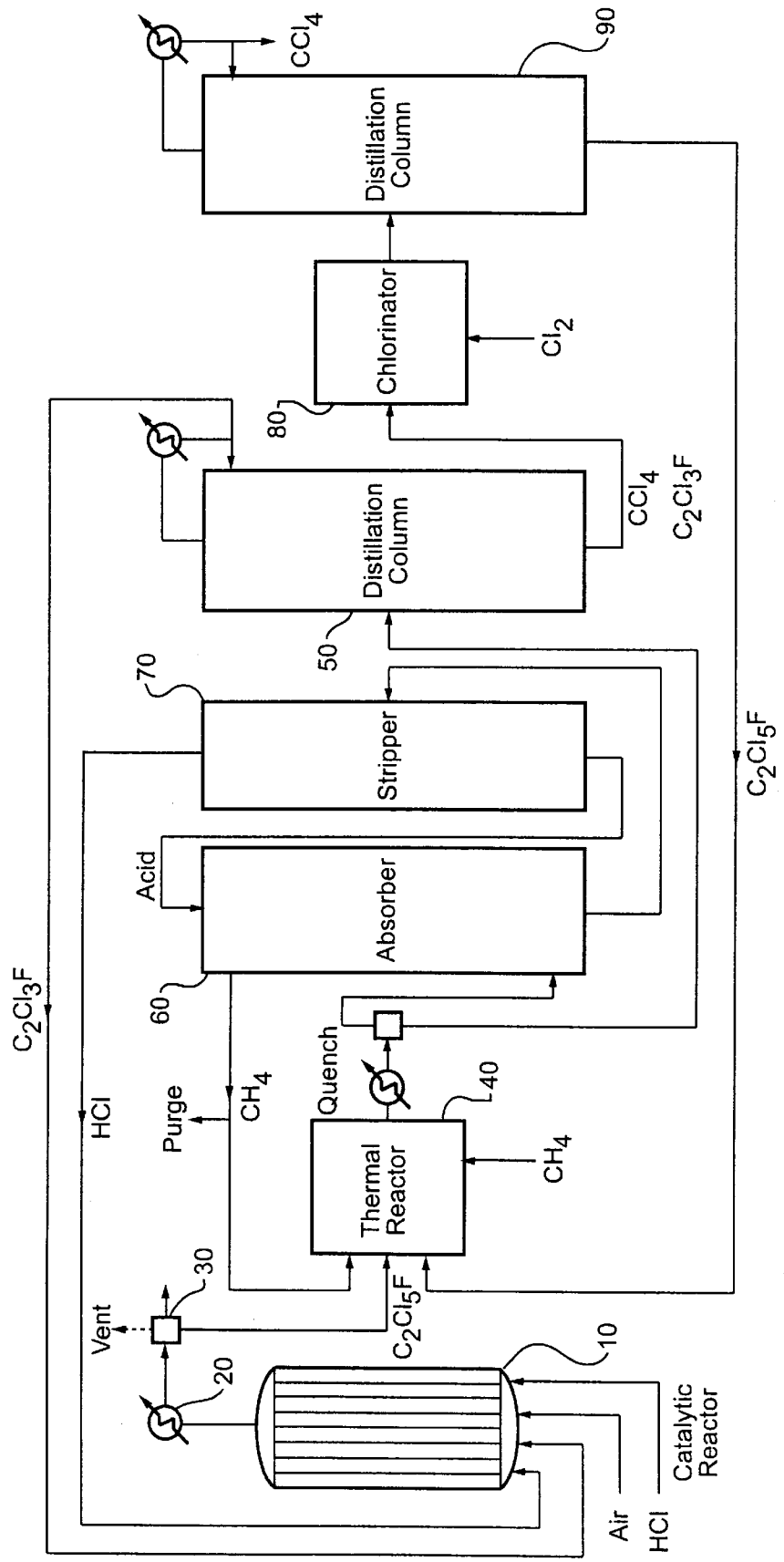
FIG. 1 is a diagrammatic representation of a preferred means for operating the present chlorination method, including a shell and tube catalytic reactor in series with a thermal reactor with means for recycling and for withdrawal of chlorinated product and fractionation.

In one preferred embodiment of the present invention, two separate reaction steps are carried out in tandem. First, an unsaturated aliphatic fluorocarbon, selected from the croup consisting of perchlorofluorocarbons and perfluorocarbons, is reacted with hydrogen chloride and oxygen in the presence of a catalyst to produce the corresponding saturated perchlorofluorocarbon and water. Second, the perchlorofluorocarbon so produced is isolated from the reaction products of the first step, and it is reacted in the vapor phase with an aliphatic hydrocarbon containing from one to four carbon atoms, thereby producing the desired chlorinated hydrocarbon plus hydrogen chloride and the original unsaturated aliphatic fluorocarbon. Both the hydrogen chloride and fluorocarbon produced in the second step are separated from the chlorinated hydrocarbon product and are recycled to the first step, which is conventionally known as oxychlorination. By this means, a continuous process is provided in which the fluorocarbon serves as a chlorine carrier.

In another preferred embodiment of the invention, air is substituted for all or part of the oxygen requirement. Also, chlorine is used to supplement or replace entirely the supply of hydrogen chloride by introducing chlorine alone with the saturated perchlorofluorocarbon to the second reaction zone. By recycling the hydrogen chloride from the second reactor to the first reactor, there is no net production of hydrogen chloride.

DETAILED DESCRIPTION OF THE PREFERRED EMBODIMENTS

The use of fluorocarbons as chlorine carriers is based on the special properties of this family of compounds. Most important, fluorocarbons are known for their relative stability although there are some exceptions to this rule. The addition of chlorine to fluorinated olefins is practically quantitative and has long been used in the separation and purification of these compounds. In another reaction, fluorinated olefins can be prepared by the elimination of vicinal chlorine atoms in saturated fluorocarbons containing two or more carbon atoms. This method, which depends on the use of a metal reagent, is commonly used in the preparation of fluorocarbon monomers.

Absent the use of metal reagents, however, saturated fluorocarbons are recognized for their inertness. Their decomposition requires the use of high temperatures, catalysts or ultraviolet radiation. Further evidence of the stability of fluorocarbons was provided by Nychka et al. in U.S. Pat. No. 4,088,704. This reference reported that although hexachloroethane will readily chlorinate hydrocarbons at 400° C., fluorinated hexachloroethane to a large extent is unreactive. Notwithstanding these findings, the present invention makes deliberate use of this reaction. The rationale for this approach is explained in the description which follows.

The reactions of the present invention are illustrated by the following equations for the preparation of methyl chloride from methane making use of trichlorofluoroethylene as the unsaturated perchlorofluorocarbon in the first step:

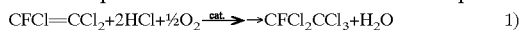  (1)

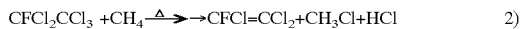  (2)

Therefore the net reaction is:

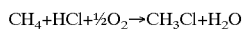

The physical properties of the specified fluorocarbons are favorable for carrying out the above reactions. Trichlorofluoroethylene has a boiling point of 71° C. and melting point of –119° C. Pentachlorofluoroethane boils at approximately 137° C. and melts at close to 100° C. Furthermore, the solubilities of these compounds in water are low.

Likewise, the chemical properties of the selected fluorocarbons are conducive to the success of the process. These compounds are comparatively nontoxic. Being stable compounds, they resist oxidation and are slow to hydrolyze. Pentachlorofluoroethane dehalogenates less readily than hexachloroethane but not to such a degree that it loses its effectiveness as a chlorinating agent.

Other fluorocarbons are candidates for use in the process. For example, one isomer of $C_3Cl_5F$ boils at 171° C. and melts at –77° C. The corresponding paraffin $C_3Cl_7F$ boils at 105° C. under 14 mm pressure and melts at 8° C. Tetrafluoroethylene has a boiling point of –76° C. and dichlorotetrafluoroethane has a boiling point of 3.6° C.

The first reaction, in which trichlorofluoroethylene was shown to be oxychlorinated to pentachlorofluoroethane employing a catalyst, may typically be carried out in a molten salt reactor, fluidized bed reactor or shell and tube reactor. These reactor types are planned to remove heat from the reaction and to minimize side reactions. The stability of perchlorofluorocarbons allows greater latitude in reactor design, thereby achieving savings in investment cost.

The temperature of the oxychlorination reaction is maintained preferably in the range from about 200° to about 395° C. The use of perchlorofluorocarbons will permit operation within this higher than normal temperature range. The catalyst of choice is copper chloride deposited on an inert support. This is the well-known Deacon catalyst which has been used experimentally to produce chlorine from hydrogen chloride and air. Various salts may be mixed with the copper chloride to promote its effectiveness, e.g., potassium chloride, ferric chloride, and lead chloride.

The second reaction is conducted in the vapor phase at an elevated temperature, preferably in the range from about 400° to about 700° C. Because of the lower reactivity of fluorocarbons as opposed to hexachloroethane, the actual temperature used will exceed what would normally be the case for hexachloroethane. The probable mechanism by which the methane is chlorinated is a series of free-radical reactions. Chlorine is released from the pentachlorofluoroethane and reacts with the methane to form methyl chloride. The dehalogenation of pentachlorofluoroethane is endothermic, whereas the chlorination of methane is exothermic. Thus, some degree of temperature control is obtained with the heat given off by one reaction being absorbed by the other.

Whether methane is the hydrocarbon or some other feed is used, such as butane, several products are possible depending on the degree of chlorination. In the case of methane chlorination, the following products are formed: methyl chloride, methylene chloride, chloroform and carbon tetrachloride. Under certain conditions, i.e., an excess of chlorinating agent and high temperatures, some perchloroethylene may also be produced.

The mix of products will depend, as already noted, on certain variables. One is temperature. Another is the ratio of pentachlorofluoroethane to methane feed. The use of an excess of methane will maximize the production of methyl chloride. The reactor design can also be a factor. By incorporating a static mixer into a tubular reactor, back-mixing can be reduced in order to control polychlorination. Finally, in the literature catalysts have been reported which can provide some degree of selectivity.

The process is designed such that there is no net production nor consumption of fluorocarbon. In this respect the process conforms to the provisions of the Montreal Protocol. which banned the use of ozone-destroying chlorofluorocarbons (CFCs) in the industrial world after Jan. 1, 1996. (*Scientific American*, December 1994, page 97, incorporated in its entirety by reference in this specification). This international treaty singled out these compounds for special treatment because of their unique chemical properties. The criteria established by the Montreal Protocol for the handling of CFCs can be met by the present invention.

The necessary steps to achieve conformance with the treaty include an extra purification of product, a scrubber to treat the vent gases, and monitors for the detection of any fluorocarbons in the exit streams. In one embodiment of the invention, crude product is subjected to addition chlorination to convert traces of unsaturated fluorocarbon to the corresponding saturated compound. This procedure is followed by a polishing distillation step in order to separate the saturated fluorocarbon from the chlorinated hydrocarbon. The saturated fluorocarbon is then recycled to the second step of the process.

Referring to the drawing, FIG. 1 is a schematic view of the operation of a preferred embodiment of the present invention. It illustrates the production of carbon tetrachloride. Air, hydrogen chloride and trichlorofluoroethylene are fed to the shell and tube catalytic reactor 10 which contains copper chloride catalyst. The oxychlorination reaction is carried out in this catalytic reactor.

The effluent stream from reactor 10 is cooled in condenser 20 to condense the vapors. The inert gases are vented while the water is decanted from the chlorinated organics in separator 30. Pentachlorofluoroethane dissolved in an excess of trichlorofluoroethylene is transferred to thermal reactor 40 where it is reacted in the vapor phase with methane feedstock.

Hot vapors from the thermal reactor are quenched, as for example, by a stream of cold trichlorofluoroethylene in order to minimize the formation of heavy ends and tars. Unreacted methane and hydrogen chloride are separated from the liquid organics which are pumped to distillation column 50. In this column carbon tetrachloride is fractionated from trichlorofluoroethylene, which is recycled back to catalytic reactor 10.

In absorber 60, hydrogen chloride gas is separated from the unreacted methane by absorption in weak hydrochloric acid. The concentrated acid exiting from the absorber is pumped to a stripper column 70, where hydrogen chloride is desorbed. Hydrogen chloride from the stripper is recycled back to catalytic reactor 10. Methane from the top of the absorber is recycled to thermal reactor 40. A purge stream is taken from the recycled methane stream in order to remove inert gases.

The crude carbon tetrachloride which is obtained from distillation column 50 may contain traces of trichlorofluoroethylene. The reason for this contamination is the closeness in the boiling points of carbon tetrachloride with B.P. of 77° C. and trichlorofluoroethylene with B.P. of 71° C. In order to effect a complete separation, the crude product is chlorinated in chlorinator 80, in which chlorine is added to the double bond of trichlorofluoroethylene. This reaction is carried out in the liquid phase using ultraviolet light to promote it. The resulting pentachlorofluoroethane with B.P. of 137° C. is separated from carbon tetrachloride in polishing distillation column 90 and then recycled to thermal reactor 40.

In practice, the intermediates methyl chloride, methylene chloride, and chloroform are formed in the thermal reactor along with carbon tetrachloride. These byproducts are separated in additional facilities (not shown) and recycled back to the thermal reactor for further chlorinatiion.

Chlorinated hydrocarbons which can be produced by the process are valuable items of commerce. By way of example, methyl chloride is used in the manufacture of silicone polymers. It has also been proposed as an intermediate in the production of methyl alcohol. Ethylene dichloride is a raw material for producing vinyl chloride resins. Allyl chloride is a reactant used in the manufacture of pharmaceuticals, resins and plastics. Butyl chloride is used in organic synthesis, e.g., in the manufacture of butyl cellulose.

What is desired to claim as my exclusive privilege and property in the invention as described is the following.

I claim:

1. A process for the chlorination of aliphatic hydrocarbons containing 1 to 4 carbon atoms to produce a chlorinated hydrocarbon using hydrogen chloride as the source of chlorine and a fluorocarbon as a chlorine carrier, said process consisting essentially of steps operated in tandem:

first, subjecting an unsaturated aliphatic fluorocarbon, selected from the group consisting of perchlorofluorocarbons and perfluorocarbons, to oxychlorination with hydrogen chloride and oxygen in the presence of a catalyst to give reaction products consisting essentially of water and the corresponding saturated perchlorofluorocarbon with reactivity lower than hexachloroethane;

second, isolating said saturated perchlorofluorocarbon from the reaction products of the first step and reacting it with an aliphatic hydrocarbon containing 1 to 4 carbon atoms in the vapor phase to produce the chlorinated hydrocarbon, hydrogen chloride and the unsaturated aliphatic fluorocarbon;

third, separating hydrogen chloride and unsaturated aliphatic fluorocarbon from the reaction products of the second step to produce a crude chlorinated hydrocarbon product, and recycling the hydrogen chloride and the unsaturated aliphatic fluorocarbon to the first step; and fourth, subjecting the crude chlorinated hydrocarbon product to addition chlorination in order to convert traces of unsaturated aliphatic fluorocarbon to the corresponding saturated perchlorofluorocarbon, separating the saturated perchlorofluorocarbon from the chlorinated hydrocarbon, and recycling the saturated perchlorofluorocarbon to the second step, thereby providing a continuous process without the production or consumption of fluorocarbon, whereby the process conforms to the provisions of the Montreal Protocol.

2. A process according to claim 1 in which the catalyst used in step 1 comprises copper chloride.

3. A process according to claim 2 wherein the copper containing catalyst is enhanced by the addition of a salt selected from the group consisting of potassium chloride, ferric chloride and lead chloride.

4. A process according to claim 1 in which the oxychlorination reaction in step 1 is carried out at temperatures in the range of about 200° to about 395° C.

5. A process according to claim 1 in which the vapor phase reaction in step 2 is carried out at temperatures in the range of about 400° to 700° C.

6. A process according to claim 1 in which the unsaturated aliphatic fluorocarbon is trichlorofluoroethylene and the corresponding saturated perchlorofluorocarbon is pentachlorofluoroethane.

7. A process according to claim 1 in which the unsaturated aliphatic fluorocarbon is tetrafluoroethylene and the corresponding saturated perchlorofluorocarbon is dichlorotetrafluoroethane.

8. A process according to claim 1 in which the chlorinated hydrocarbon is methyl chloride.

9. A process according to claim 8 in which the methyl chloride is an intermediate used in the production of methyl alcohol.

* * * * *